United States Patent
Miao

(10) Patent No.: US 10,238,758 B2
(45) Date of Patent: *Mar. 26, 2019

(54) RADIOLABELED ALPHA-MELANOCYTE STIMULATING HORMONE HYBRID PEPTIDE FOR MELANOMA TARGETING

(71) Applicant: STC.UNM, Albuquerque, NM (US)

(72) Inventor: Yubin Miao, Englewood, CO (US)

(73) Assignee: STC.UNM, Albuquerque, NM (US)

( * ) Notice: Subject to any disclaimer, the term of this patent is extended or adjusted under 35 U.S.C. 154(b) by 77 days.

This patent is subject to a terminal disclaimer.

(21) Appl. No.: 15/261,890

(22) Filed: Sep. 10, 2016

(65) Prior Publication Data

US 2017/0087259 A1 Mar. 30, 2017

Related U.S. Application Data

(63) Continuation of application No. 13/617,042, filed on Sep. 14, 2012, now Pat. No. 9,463,255.

(60) Provisional application No. 61/540,814, filed on Sep. 29, 2011.

(51) Int. Cl.
| | |
|---|---|
| *A61K 51/00* | (2006.01) |
| *A61M 36/14* | (2006.01) |
| *A61K 51/08* | (2006.01) |
| *C07K 7/56* | (2006.01) |
| *A61K 38/17* | (2006.01) |
| *A61K 38/00* | (2006.01) |

(52) U.S. Cl.
CPC ............ *A61K 51/086* (2013.01); *A61K 38/17* (2013.01); *A61K 51/082* (2013.01); *C07K 7/56* (2013.01); *A61K 38/00* (2013.01)

(58) Field of Classification Search
CPC .... A61K 51/00; A61K 51/082; A61K 51/086; A61K 38/00; A61K 38/17; C07K 7/56
USPC ........ 424/1.11, 1.65, 1.69, 9.1, 9.2, 9.3, 9.4, 424/9.6; 514/1, 1.1, 9.7, 10.7, 19.2, 19.3, 514/19.4, 19.5, 19.6, 21.1, 21.4; 530/300, 530/304, 312, 317, 326, 333, 338
See application file for complete search history.

(56) References Cited

U.S. PATENT DOCUMENTS

| | | | | |
|---|---|---|---|---|
| 6,607,709 | B1* | 8/2003 | Jurisson | A61K 51/08 424/1.11 |
| 7,919,118 | B2* | 4/2011 | Holmes | C07K 14/505 424/486 |
| 8,986,651 | B2* | 3/2015 | Miao | A61K 51/088 424/1.69 |
| 9,005,575 | B2* | 4/2015 | Miao | A61K 51/088 424/1.11 |
| 9,463,255 | B1* | 10/2016 | Miao | A61K 51/086 |
| 2012/0107237 | A1 | 5/2012 | Miao et al. | |

FOREIGN PATENT DOCUMENTS

WO 2011005380 A2 1/2011

OTHER PUBLICATIONS

Yang et al Nuclear Medicine and Biology, vol. 37, pp. 873-883. (Year: 2010).*
Jemal A, Siegel R, Xu J, Ward E. Cancer statistics. CA Cancer J Clin 2010;60:277-300.
Giblin MF, Wang N, Hoffman TJ, Jurisson SS, Quinn TP. Design and characterization of alpha-melanotropin peptide analogs cyclized through rhenium and technetium metal coordination. Proc Natl Acad Sci USA 1998;95:12814-8.
Froidevaux S, Calame-Christe M, Tanner H, Sumanovski L, Eberle AN. A novel DOTA-alpha-melanocyte-stimulating hormone analog for metastatic melanoma diagnosis. J Nucl Med 2002;43:1699-706.
Miao Y, Whitener D, Feng W, Owen NK, Chen J, Quinn TP. Evaluation of the human melanoma targeting properties of radiolabeled alpha-melanocyte stimulating hormone peptide analogues. Bioconjug Chem 2003;14:1177-84.
Froidevaux S, Calame-Christe M, Schuhmacher J, Tanner H, Saffrich R, Henze M. et al. A gallium-labeled DOTA-alpha-melanocyte-stimulating hormone analog for PET imaging of melanoma metastases. J Nucl Med 2004;45:116-23.
McQuade P, Miao Y, Yoo J, Quinn TP, Welch MJ, Lewis JS. Imaging of melanoma using 64Cu- and 86Y-DOTA-ReCCMSH(Arg11), a cyclized peptide analogue of alpha-MSH. J Med Chem 2005;48:2985-92.
Wei L, Butcher C, Miao Y, Gallazzi F, Quinn TP, Welch MJ, et al. Synthesis and biologic evaluation of 64Cu-labeled rhenium-cyclized alpha-MSH peptide analog using a cross-bridged cyclam chelator. J Nucl Med 2007;48:64-72.
Cheng Z, Xiong Z, Subbarayan M, Chen X, Gambhir SS. 64Cu-labeled alpha-melanocyte-stimulating hormone analog for MicroPET imaging of melanocortin 1 receptor expression. Bioconjug Chem 2007;18:765-72.
Miao Y, Benwell K, Quinn TP. 99mTc- and 111In-labeled alpha-melanocyte-stimulating hormone peptides as imaging probes for primary and pulmonary metastatic melanoma detection. J Nucl Med 2007;48:73-80.

(Continued)

*Primary Examiner* — D. L. Jones
(74) *Attorney, Agent, or Firm* — Henry D. Coleman; R. Neil Sudol

(57) ABSTRACT

The present invention is directed to novel non-invasive diagnostic tools/compounds to image cancers, especially, melanoma, including metastatic melanoma in vivo. The present compounds exhibit enhanced uptake in cancerous cells and tissue, suggesting favorable selective activity of compounds according to the present invention, which can be used as effective therapeutic agents against melanoma, including metastatic melanoma. The compounds according to the present invention represent an advance in the diagnosis and treatment of melanoma, including metastatic melanoma using non-invasive molecular imaging techniques. The novel probes of the present invention are useful to initiate therapy for melanoma as well as monitor patients' response to chemotherapy treatments and other interventions or therapies used in the treatment of melanoma/metastatic melanoma. Compounds according to the present invention may be used as diagnostic and therapeutic tools for a number of conditions and diseases states, especially melanoma.

19 Claims, 7 Drawing Sheets

(56) References Cited

OTHER PUBLICATIONS

Miao Y, Figueroa SD, Fisher DR, Moore HA, Testa RF, Hoffman TJ, et al. 203Pb-labeled alpha-melanocyte-stimulating hormone peptide as an imaging probe for melanoma detection. J Nucl Med 2008;49:823-9.

Miao Y, Gallazzi F, Guo H, Quinn TP. 111In-labeled lactam bridge-cyclized alpha-melanocyte stimulating hormone peptide analogues for melanoma imaging. Bioconjug Chem 2008;19:539-47.

Guo H, Shenoy N, Gershman BM, Yang J, Sklar LA, Miao Y. Metastatic melanoma imaging with an 111In-labeled lactam bridge-cyclized alpha-melanocyte stimulating hormone peptide. Nucl Med Biol 2009;36:267-76.

Guo H, Yang J, Gallazzi F, Miao Y. Reduction of the ring size of radiolabeled lactam bridge-cyclized alpha-MSH peptide resulting in enhanced melanoma uptake. J Nucl Med 2010;51:418-26.

Guo H, Yang J, Gallazzi F, Miao Y. Effects of the amino acid linkers on melanoma-targeting and pharmacokinetic properties of Indium-111-labeled lactam bridge-cyclized α-MSH peptides. J Nucl Med 2011;52:608-16.

Haubner R, Wester HJ, Reuning U, Senekowitsch-Schmidtke R, Diefenbach B, Kessler H, et al. Radiolabeled alpha(v) beta(3) integrin antagonists: a new class of tracers for tumor targeting. J Nucl Med 1999;40:1061-71.

Poethko T, Schottelius M, Thumshirn G, Hersel U, Herz M, Henriksen G, et al. Two-step methodology for high-yield routine radiohalogenation of peptides: 18F-labeled RGD and octreotide analogs. J Nucl Med 2004;45:892-902.

Li C, Wang W, Wu Q, Ke S, Houston J, Sevick-Muraca E, et al. Dual optical and nuclear imaging in human melanoma xenografts using a single targeted imaging probe. Nucl Med Biol 2006;33:349-58.

Decristoforo C, Faintuch-Linkowski B, Rey A, von Guggenberg E, Rupprich M, Hernandez-Gonzales I, et al. [99mTc] HYNIC-RGD for imaging integrin alphavbeta3 expression. Nucl Med Biol 2006;33:945-52.

Alves S, Correia JD, Gano L, Rold TL, Prasanphanich A, Haubner R, et al. In vitro and in vivo evaluation of a novel 99mTc(CO)3-pyrazolyl conjugate of cyclo-(Arg-Gly-Asp-d-Tyr-Lys). Bioconjug Chem 2007;18:530-7.

Decristoforo C, Hernandez Gonzalez I, Carlsen J, Rupprich M, Huisman M, Virgolini I, et al. 68Ga- and 111In-labelled DOTA-RGD peptides for imaging of alpha(v)beta(3) integrin expression. Eur J Nucl Med Mol Imaging 2008;35:1507-15.

Hultsch C, Schottelius M, Auernheimer J, Alke A, Wester HJ. 18F-Fluoroglucosylation of peptides, exemplified on cyclo (RGDfK). Eur J Nucl Med Mol Imaging 2009;36:1469-74.

Wei L, Ye Y, Wadas TJ, Lewis JS, Welch MJ, Achilefu S, et al. 64Cu-labeled CB-TE2A and diamsar-conjugated RGD peptide analogs for targeting angiogenesis: comparison of their biological activity. Nucl Med Biol 2009;36:277-85.

Yang J, Guo H, Miao Y. Technetium-99m-labeled Arg-Gly-Asp-conjugated alpha-melanocyte stimulating hormone hybrid peptides for human melanoma imaging. Nucl Med Biol 2010;37:873-83.

Yang J, Guo H, Gallazzi F, Miao Y. Evaluation of a novel Arg-Gly-Asp-conjugated alpha-melanocyte stimulating hormone hybrid peptide for potential melanoma therapy. Bioconjug Chem 2009;20:1634-42.

Mathews and van Holde, Biochemistry, 1990, p. 136.

Yang J, et al. Linker modification reduced the renal uptake of technetium-99m-labeled Arg-Ala-Asp-conjugated alpha-melanocyte stimulating hormone peptide. Bioorganic & Medicinal Chemistry Letters, 2014;24: 195-198.

Yang J, Miao Y. Substitution of Gly with Ala enhanced the melanoma uptake of technetium-99m-labeled Arg-Ala-Asp-conjugated alpha-melanocyte stimulating hormone peptide. Bioorganic & Medicinal Chemistry Letters, 2012;22:1541-1545.

Flook AM, et al. Effects of Amino Acids on Melanoma Targeting and Clearance Properties of Tc-99m-Labeled Arg-X-Asp-Conjugated alpha-Melanocyte Stimulating Hormone Peptides. J Med Chem, 2013;56:8793-8802.

Flook AM, et al. Substitution of the Lys Linker with the Beta-Ala Linker Dramatically Decreased the Renal Uptake of 99m-Tc-Labeled Arg-X-Asp-Conjugated and X-Ala-Asp-Conjugated alpha-Melanocte Stimulating Hormone Peptides. J MedChem,, 2014;57:9010-9018.

Flook AM, et al. Evaluation of New Tc-99m-Labled Arg-X-Asp-Conugated alpha-Melanocyte Stimulating Hormone Peptides for Melanoma Imaging. Mol Pharmaceutics, 2013;10:3417-3424.

* cited by examiner

FIGURE 7

| Tissue | 0.5 h | 2 h | 4 h | 24 h | 2 h NDP blockade | 2 h L-lysine co-injection |
|---|---|---|---|---|---|---|
| | | | Percent injected dose/gram (%ID/g) | | | |
| Tumor | 16.65 ± 1.91 | 19.91 ± 4.02 | 18.01 ± 3.51 | 9.24 ± 3.63 | 1.55 ± 0.71* | 18.62 ± 1.73 |
| Brain | 0.14 ± 0.03 | 0.04 ± 0.01 | 0.02 ± 0.00 | 0.02 ± 0.01 | 0.02 ± 0.02 | 0.04 ± 0.01 |
| Blood | 3.46 ± 0.50 | 0.49 ± 0.31 | 0.20 ± 0.09 | 0.05 ± 0.02 | 0.67 ± 0.17 | 0.44 ± 0.11 |
| Heart | 2.12 ± 0.46 | 0.32 ± 0.13 | 0.20 ± 0.08 | 0.13 ± 0.04 | 0.32 ± 0.15 | 0.30 ± 0.10 |
| Lung | 3.91 ± 1.37 | 0.87 ± 0.21 | 0.46 ± 0.11 | 0.29 ± 0.07 | 1.49 ± 0.37 | 0.78 ± 0.17 |
| Liver | 2.66 ± 0.17 | 2.22 ± 0.39 | 1.80 ± 0.51 | 1.25 ± 0.20 | 4.17 ± 1.36 | 1.46 ± 0.08 |
| Skin | 4.71 ± 0.49 | 0.71 ± 0.25 | 0.34 ± 0.05 | 0.26 ± 0.15 | 0.85 ± 0.58 | 0.58 ± 0.10 |
| Spleen | 1.54 ± 0.41 | 0.48 ± 0.21 | 0.37 ± 0.26 | 0.39 ± 0.24 | 0.58 ± 0.72 | 0.50 ± 0.09 |
| Stomach | 2.50 ± 0.16 | 1.61 ± 0.35 | 1.09 ± 0.37 | 0.51 ± 0.22 | 2.37 ± 0.35 | 1.92 ± 0.24 |
| Kidneys | 127.41 ± 17.32 | 92.97 ± 21.72 | 98.56 ± 13.49 | 33.19 ± 3.39 | 74.13 ± 16.15 | 50.10 ± 18.56* |
| Muscle | 0.72 ± 0.18 | 0.14 ± 0.08 | 0.18 ± 0.04 | 0.08 ± 0.04 | 0.32 ± 0.04 | 0.28 ± 0.30 |
| Pancreas | 0.95 ± 0.38 | 0.19 ± 0.05 | 0.12 ± 0.05 | 0.02 ± 0.07 | 0.23 ± 0.09 | 0.14 ± 0.04 |
| Bone | 1.75 ± 0.29 | 0.37 ± 0.21 | 0.17 ± 0.08 | 0.11 ± 0.08 | 0.40 ± 0.27 | 0.52 ± 0.31 |
| | | | Percent injected dose (%ID) | | | |
| Intestines | 2.15 ± 0.25 | 1.50 ± 0.86 | 1.55 ± 0.42 | 0.85 ± 0.42 | 3.89 ± 1.31 | 1.31 ± 0.31 |
| Bladder | 30.95 ± 5.12 | 65.84 ± 7.08 | 65.69 ± 4.62 | 85.62 ± 1.21 | 69.54 ± 0.63 | 70.34 ± 3.28 |
| | | | Uptake ratio of tumor/normal tissue | | | |
| Tumor/Blood | 4.81 | 40.63 | 90.05 | 184.80 | 2.31 | 42.32 |
| Tumor/Kidneys | 0.13 | 0.21 | 0.18 | 0.28 | 0.02 | 0.37 |
| Tumor/Lung | 4.26 | 22.89 | 39.15 | 31.86 | 1.04 | 23.87 |
| Tumor/Liver | 6.26 | 8.97 | 10.01 | 7.39 | 0.37 | 12.75 |
| Tumor/Muscle | 23.13 | 142.21 | 100.06 | 115.50 | 4.84 | 66.50 |

RADIOLABELED ALPHA-MELANOCYTE STIMULATING HORMONE HYBRID PEPTIDE FOR MELANOMA TARGETING

This application claims the benefit of priority of U.S. provisional application Ser. No. U.S. 61/540,814, filed Sep. 29, 2011, which application is incorporated by reference in its entirety herein.

RELATED APPLICATIONS AND GOVERNMENT SUPPORT

The present invention was made with Government support under grant no. NM-INBRE P20RR016480 from the United States NIH. Consequently, the U.S. government has certain rights in the invention.

FIELD OF THE INVENTION

The present invention is directed to novel non-invasive diagnostic tools/compounds to image cancers, especially, melanoma, including metastatic melanoma in vivo. The present compounds exhibit enhanced uptake in cancerous cells and tissue, suggesting favorable selective activity of compounds according to the present invention. The compounds according to the present invention represent an advance in the diagnosis and treatment of melanoma, including metastatic melanoma using non-invasive molecular imaging techniques. The novel probes of the present invention will also be useful to initiate therapy for melanoma as well as monitor patients' response to chemotherapy treatments and other interventions or therapies used in the treatment of melanoma/metastatic melanoma. Compounds according to the present invention may be used as diagnostic and therapeutic tools for a number of conditions and diseases states, especially melanoma.

BACKGROUND OF THE INVENTION

Melanoma is the most deadly skin cancer with an increasing incidence [1]. Over the past decade, it has been of interest to develop receptor-targeting radiolabeled peptides for melanoma imaging since early diagnosis followed by prompt surgical removal is a patient's best opportunity for a cure. Due to the over-expression on melanoma, both melanocotin-1 (MC1) and $\alpha_v\beta_3$ integrin receptors have been used as targets for radiolabeled alpha-melanocyte stimulating hormone ($\alpha$-MSH) [2-14] and Arg-Gly-Asp (RGD) peptides [15-22], respectively. Recently, the inventors have developed a novel RGD-conjugated $\alpha$-MSH hybrid peptide targeting both MC1 and $\alpha_v\beta_3$ integrin receptors for M21 human melanoma imaging [23]. The cyclic RGD {Arg-Gly-Asp-DTyr-Asp} motif was conjugated to [Cys$^{3,4,10}$, D-Phe$^7$, Arg$^{11}$]$\alpha$-MSH$_{3-13}$} peptide via a lysine linker to yield RGD-Lys-(Arg$^{11}$)CCMSH peptide. Meanwhile, the inventors designed two control peptides namely RAD-Lys-(Arg$^{11}$)CCMSH and RGD-Lys-(Arg$^{11}$)CCMSH scramble for comparison. The in vitro results revealed that the switch from RGD to RAD in the hybrid peptide decreased the $\alpha_v\beta_3$ integrin receptor binding affinity by 248-fold, whereas the scramble of CCMSH moiety in the hybrid peptide sacrificed the MC1 receptor binding affinity by 100-fold. The biodistribution results demonstrated that targeting both MC1 and $\alpha_v\beta_3$ integrin receptors enhanced the melanoma uptake of $^{99m}$Tc-RGD-Lys-(Arg$^{11}$)CCMSH in M21 human melanoma xenografts. The xenografted M21 human melanoma lesions were clearly visualized using $^{99m}$Tc-RGD-Lys-(Arg$^{11}$)CCMSH as an imaging probe [23].

While the switch from RGD to RAD in the hybrid peptide decreased the $\alpha_v\beta_3$ integrin receptor binding affinity by 248-fold, surprisingly, the inventors found that the switch from RGD to RAD in the hybrid peptide dramatically increased the MC1 receptor binding affinity of RAD-Lys-(Arg$^{11}$)CCMSH compared to RGD-Lys-(Arg$^{11}$)CCMSH (0.3 vs. 2.0 nM) in M21 melanoma cells [23]. Therefore, the inventors were interested in investigating whether such change in MC1 receptor binding affinity could result in enhanced melanoma uptake of $^{99m}$Tc-RAD-Lys-(Arg$^{11}$)CCMSH compared to $^{99m}$Tc-RGD-Lys-(Arg$^{11}$)CCMSH. Thus, the inventors examined the receptor binding affinity of RAD-Lys-(Arg$^{11}$)CCMSH, internalization and efflux properties of $^{99m}$Tc-RAD-Lys-(Arg$^{11}$)CCMSH in B16/F1 melanoma cells. Furthermore, the inventors determined the melanoma targeting and imaging properties of $^{99m}$Tc-RAD-Lys-(Arg$^{11}$)CCMSH in B16/F1 melanoma-bearing C57 mice. The results proved to be unexpectedly favorable to prior art compounds.

BRIEF DESCRIPTION OF THE INVENTION

The present invention relates to compounds according to the general structure:

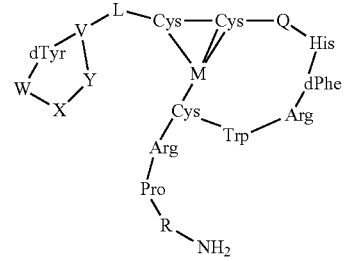

Where Q is an amino acid unit selected from the group consisting of glutamic acid and aspartic acid, preferably glutamic acid;
R is an amino acid unit selected from the group consisting of valine, threonine, leucine, and isoleucine, preferably valine;
V is an amino acid residue selected from the group consisting of aspartic acid and glutamic acid, preferably aspartic acid;
W is an amino acid selected from the group consisting of aspartic acid and glutamic acid, preferably aspartic acid;
X is an amino acid residue selected from the group consisting of alanine, valine threonine, leucine, isoleucine, serine, aspartic acid and glutamic acid, preferably alanine;
Y is an amino acid residue selected from the group consisting of arginine, lysine, alanine, valine, threonine, leucine, isoleucine, serine, aspartic acid and glutamic acid, preferably arginine;
L is absent, a single amino acid selected from the group consisting of glycine, alanine, β-alanine, lysine and arginine, or a linker group according to the formula:

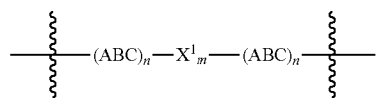

Where each $X^1$ is independently an amino acid residue (preferably, for example, an amino acid group which is neutral (e.g. a neutral amino acid such as norleucine (Nle), leucine, isoleucine, glycine or alanine) or is positively charged at physiological pH (arginine, lysine) and is preferably selected from the group consisting of glycine, alanine, arginine or lysine, or is an amino acid linker comprising an alkylene group which is optionally substituted with one or more $C_1$-$C_3$ alkyl or $C_1$-$C_3$ alkanol group(s) or an ethylene glycol containing group according to the chemical structures:

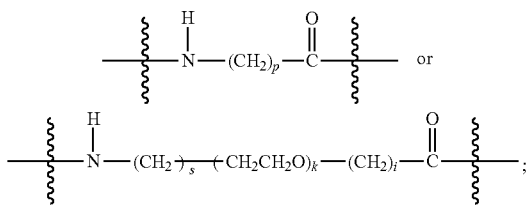

Where ABC is an amino acid linker wherein A is absent or is a neutral or positively charged amino acid at physiological pH;
B is a neutral or positively charged amino acid at physiological pH;
C is absent or is a neutral or negatively charged amino acid at physiological pH;
m is an integer from 0 to 250, from 1 to 100, often 0 to 5, preferably 0 or 1;
each n is independently 0 or 1, preferably at least one n is 0 when m is 1 or more;
p is an integer from 0 to 20, often 0 to 10, often 1-8, often 2-5;
k is an integer from 0 to 10, preferably 1 or 2;
i is an integer from 0 to 10, often 1 or 2;
s is an integer from 0 to 10, often 0, 1 or 2, more often 0; and
M is a radioisotope, preferably a polyvalent cationic radioisotope, even more preferably selected from the group consisting of $^{86}Y$, $^{90}Y$, $^{111}In$, $^{177}Lu$, $^{225}Ac$, $^{212}Bi$, $^{213}Bi$, $^{66}Ga$, $^{67}Ga$, $^{68}Ga$, $^{64}Cu$, $^{67}Cu$, $^{71}As$, $^{72}As$, $^{76}As$, $^{77}As$, $^{65}Zn$, $^{48}V$, $^{203}Pb$, $^{209}Pb$, $^{212}Pb$, $^{166}Ho$, $^{149}Pm$, $^{153}Sm$, $^{201}Tl$, $^{188}Re$, $^{186}Re$, and $^{99m}Tc$, or
a pharmaceutically acceptable salt thereof.
Preferred compounds according to the present invention are represented by the chemical formula:

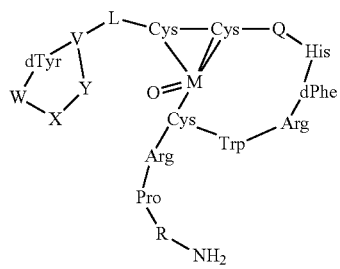

Where Q is glutamic acid;
R is valine;
V is aspartic acid;
W is aspartic acid;
X is alanine;
Y is arginine;

L is absent, a single amino acid selected from the group consisting of glycine, alanine, β-alanine, lysine and arginine, or a

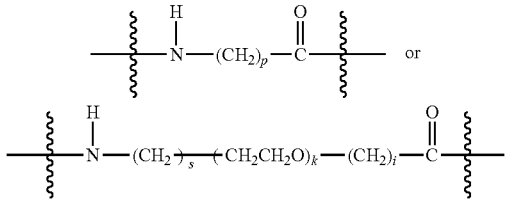

group,
Where p is an integer 0-6, often 1-5;
k is an integer from 0 to 20, often 1-5, more often 1 or 2;
i is an integer from 0 to 10, often 0, 1 or 2, more often 0;
s is an integer from 0 to 10, often 0, 1 or 2, more often 0; and
M is $^{99m}Tc$ or
a pharmaceutically acceptable salt thereof.

Radioisotopes are selected based on the physical half life, the decay mode (alpha, beta, auger, gamma, X-ray) and the energy of the radioisotope. In diagnostic aspects of the present invention, preferred radioisotopes include, for example, $^{111}In$, $^{86}Y$, $^{86}Ga$, $^{67}Ga$, $^{68}Ga$, $^{203}Pb$, $^{64}Cu$ and $^{99m}Tc$.

Where compounds are to be analyzed using positron emission tomography or PET imaging they are labeled with a positron emitting radioisotopes such as: $^{66}Ga$, $^{68}Ga$, $^{64}Cu$, $^{86}Y$, or other polyvalent, cationic radiometals that decay by positron emission. In alternative embodiments, the compounds may be analyzed using single photon emission computed tomography or SPECT imaging when labeled with a gamma radiation emitting radioisotope which preferably includes $^{111}In$, $^{67}Ga$, $^{99m}Tc$ and $^{203}Pb$ or other gamma emitting radioisotope as disclosed herein.

The present invention relates to compounds and/or compositions which may be used to prepare imaging/therapeutic agents or as imaging/therapeutic agents (when complexed with a radioisotope) for diagnosing and treating melanoma, including metastatic melanoma as otherwise described herein. Compounds according to the present invention which are complexed with an appropriate radioisotope may be used to diagnose the existence and/or extent of melanoma, including metastatic melanoma, monitor therapy as a therapeutic aid of melanoma, including metastatic melanoma, and in certain instances, function as a therapeutic agent (peptide targeted radiation) for the treatment of melanoma, including metastatic melanoma.

The present invention also relates to pharmaceutical compositions comprising an effective amount of a compound according to the present invention which has been complexed with a radioisotope and combined with a carrier, additive or excipient in pharmaceutical dosage form as a diagnostic imaging agent or as a therapeutic agent. Compositions according to the present invention are formulated in pharmaceutical dosage form for administration preferably by a parenteral, preferably an intravenous route. Compositions according to the present invention may also be formulated for administration via a topical route, directly to the skin. Oral compositions may also be formulated for use in the present invention.

In the diagnostic method according to the present invention, a compound according to the present invention is administered to a patient, and evidence of elevated expression of MSH (especially MC1) receptors in tissue of said patient through standard well-known nuclear imaging techniques, especially radiation (radionuclide) imaging, including scintigraphic imaging, and especially single photon emission computed tomography (SPECT) and positron emission tomography (PET) in comparison to a normal standard, is indicative of a disease state (melanoma) and extent of disease state (metastasis) in the tissue of the patient. The nuclear imaging techniques useful in the present diagnostic methods are well known in the art. In general, elevated levels of radiation emanating from a diagnosed tissue is evidence of elevated MSH (including MC1) receptor activity and indicative of a disease state or condition (melanoma and/or metastatic melanoma) wherein these receptors are found at elevated levels. Methods of diagnosing the existence and/or extent (stage) of melanoma, including metastatic melanoma are therefore additional aspects of the present invention. Thus, a diagnostic method of diagnosing the existence or absence of melanoma in a patient at risk for melanoma comprises administering to said patient a compound according to the present invention; imaging said patient to determine if tissue in said patient exhibits elevated expression of MSH (especially MC1) receptors; and diagnosing said patient as having melanoma, including metastatic melanoma if said tissue evidences elevated expression of MSH (especially MC1) receptors in comparison to a standard.

Methods of monitoring the treatment of melanoma, including metastatic melanoma in conjunction with traditional or experimental melanoma therapy is an additional aspect of the invention. In this aspect, a patient's response to therapy is monitored using the methods according to the present invention. In this method, a patient is monitored before and after therapy by administering compound according to the present invention and determining (through imaging diagnostics as otherwise described herein) the extent of expression of melanocyte stimulating hormone receptors (especially MC1 receptors) in tissues of a patient before therapy and after therapy and comparing the expression levels with each other and/or with a standard (predetermined value) to determine the extent of reduction of cancer tissue which occurred pursuant to the therapeutic intervention.

Methods of treating melanoma represent a further aspect of the invention. In this aspect, compounds according to the present invention as described above are administered to a patient known to have melanoma and/or metastatic melanoma in effective amounts in order to reduce cancer tissue and otherwise treat the patient's cancer through targeted radiation therapy. The present therapeutic methods may be used alone or in combination with other treatment methods (surgery, chemotherapy, radiation therapy and/or immunotherapy (IL-2 and α-interferon) for melanoma/metastatic melanoma as otherwise disclosed herein. In preferred therapeutic method aspects of the present invention, compounds according to the present invention are labeled with $^{90}$Y, $^{177}$Lu, $^{186}$Re, $^{188}$Re, $^{212}$Bi/$^{212}$Pb, $^{213}$Bi, $^{149}$Pm, $^{166}$Ho and $^{153}$Sm, often $^{186}$Re and $^{188}$Re, and are administered to the patient (preferably intravenously or topically—i.e, directly onto the melanoma tissue in the skin of the patient) in order to target the malignant melanoma tumor, including metastatic melanoma tissue with radiation therapy. Compounds according to the present invention, because of their selective binding to MC1 receptors and their residence in melanoma cells provide for enhanced diagnostic and therapeutic methods over compounds which are known in the art.

BRIEF DESCRIPTION OF THE FIGURES

FIG. 7, Table 1 shows the biodistribution of $^{99m}$Tc-RAD-Lys-(Arg[11])CCMSH in B16/F1 melanoma-bearing C57 mice. The data was presented as percent injected dose/gram or as percent injected dose (mean±SD, n=5)

DETAILED DESCRIPTION OF THE INVENTION

Figure 1:
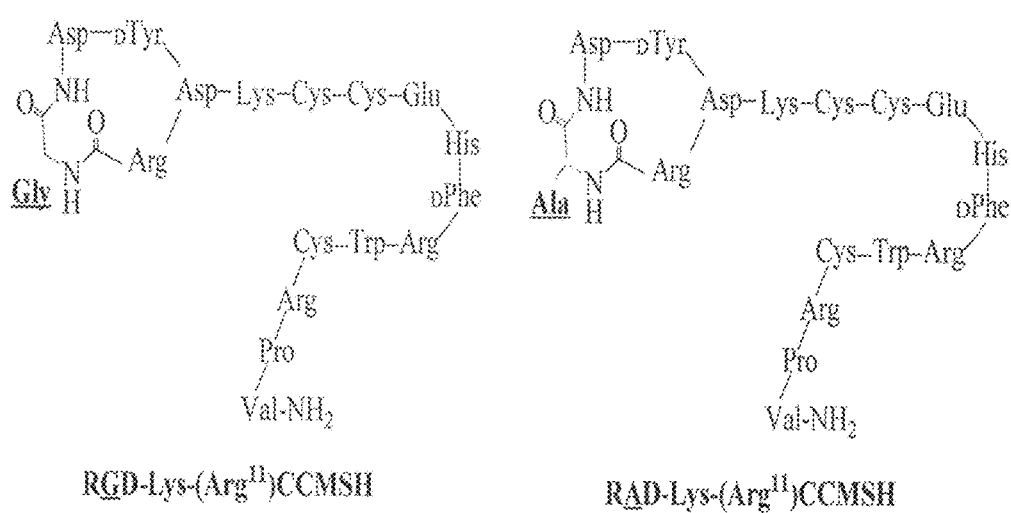
FIG. 1 shows the schematic structures of RAD-Lys-(Arg[11])CCMSH and RGD-Lys-(Arg[11])CCMSH.

The following terms are used to describe the present invention. In the event that a term is not specifically defined herein, that term is accorded its commonly understood meaning within the context of its use by those of ordinary skill in the art. It is understood that the definitions of the terms which are used to describe the present invention are interpreted in a manner consistent with the present invention and within the context of a particular term's use in describing the present invention in one or more embodiments.

As used herein and in the appended claims, the singular forms "a," "an," and "the" include plural reference unless the context clearly dictates otherwise. Thus, for example, a reference to "a compound", within context, includes a plurality (for example, two or more compounds) of such elements, and so forth. Under no circumstances is the patent be interpreted to be limited to the specific examples or embodiments or methods specifically disclosed herein.

The term "patient" or "subject" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal.

The term "compound" is used herein to refer to any specific chemical compound disclosed herein. Within its use in context, the term generally refers to a single oligopeptide which is optionally complexed with a radioisotope, but in certain instances may also refer to components/portions of such compounds, intermediates used to synthesize such compounds, stereoisomers and/or optical isomers (including racemic mixtures) of disclosed compounds. The term compound shall include, where applicable, any and all relevant pharmaceutically acceptable salts thereof.

The term "neutral amino acid" is an amino acid which has an uncharged sidechain at physiological pH. Neutral amino acids for use in the present invention include, for example, glycine, alanine, valine, leucine, isoleucine, norleucine, methionine, phenylalanine, serine, threonine and tyrosine. Preferred neutral amino acids include glycine, alanine, valine, leucine, isoleucine and norleucine. The term "positively charged amino acid" is an amino acid which has a positively charged sidechain at physiological pH. Preferred positively charged amino acids for use in the present invention include arginine and lysine.

The term "radical" is used to describe a group which is covalently bonded to another group in compounds according to the present invention.

The term "melanoma" is used to describe a malignant tumor of melanocytes which are found predominantly in skin but also in the bowel and the eye (see uveal melanoma), even though melanoma can be found in any part of the body. Melanoma is a form of cancer that begins in melanocytes, the cells that make skin pigment, or melanin. It may begin in a mole (skin melanoma), but can also begin in other pigmented tissues. There are several types of melanoma, defined by where they first appear, including skin and eye melanoma and in rare instances in the GI tract or lymph nodes Melanoma is one of the rarer types of skin cancer but causes the majority of skin cancer related deaths. Malignant melanoma is a serious type of skin cancer. It is due to uncontrolled growth of pigment cells, called melanocytes. Despite many years of intensive laboratory and clinical research, the sole effective cure is surgical resection of the primary tumor before it achieves a Breslow thickness greater than 1 mm.

Around 160,000 new cases of melanoma are diagnosed worldwide each year. About 48,000 melanoma related deaths occur worldwide per year. Malignant melanoma accounts for 75 percent of all deaths associated with skin cancer. The treatment includes surgical removal of the tumor; adjuvant treatment; chemo- and immunotherapy, or radiation therapy. The severity of melanoma is often characterized by the Clark level, which are for thin tumors and describe how deeply the cancer has spread into the skin, and the Breslow depth, which refers to the microscopic depth of tumor invasion.

The following stages are identified in the progression of the melanoma disease state. Melanoma progresses from an early stage (in situ) through an invasive stage, a high risk melanoma stage, a regional metastatic stage and a distant metastatic stage with varying degrees of survivability, as set forth below.
Melanoma Stages:
Stage 0: Melanoma in Situ (Clark Level I), 99.9% Survival
Stage I/II: Invasive Melanoma, 85-95% Survival
  T1a: Less than 1.00 mm primary, w/o Ulceration, Clark Level II-III
  T1b: Less than 1.00 mm primary, w/o Ulceration or Clark Level IV-V
  T2a: 1.00-2.00 mm primary, w/o Ulceration
Stage II: High Risk Melanoma, 40-85% Survival
  T2b: 1.00-2.00 mm primary, w/o Ulceration
  T3a: 2.00-4.00 mm primary, w/o Ulceration
  T3b: 2.00-4.00 mm primary, w/o Ulceration
  T4a: 4.00 mm or greater primary w/o Ulceration
  T4b: 4.00 mm or greater primary w/o Ulceration
Stage III: Regional Metastasis, 25-60% Survival
  N1: Single Positive Lymph Node
  N2: 2-3 Positive Lymph Nodes OR Regional Skin/In-Transit Metastasis
  N3: 4 Positive Lymph Nodes OR Lymph Node and Regional Skin/In Transit Metastases
Stage IV: Distant Metastasis, 9-15% Survival
  M1a: Distant Skin Metastasis, Normal LDH
  M1b: Lung Metastasis, Normal LDH
  M1c: Other Distant Metastasis OR Any Distant Metastasis with Elevated LDH
Based Upon AJCC 5-Year Survival with Proper Treatment Tradition therapy of melanoma involves a number of treatment options. These generally include surgery, chemotherapy, radiation therapy and immunotherapy (IL-2, other). In the case of surgery, treatment can vary and can include local excision, wide local excision, lymphadenectomy, sentinel lymph node biopsy and skin grafting. In the case of chemotherapy, a standard chemotherapeutic agent dacarbazine (DTIC) is administered to the patient in order to treat the cancer, generally through cancer cell death. In the case of radiation therapy, radiation is used as a palliative rather than a cure for melanoma. Radiation relieves bone pain and other symptoms caused by metastases to the bones, brain, and organs such as the liver. Although not curative, radiation treatment is being investigated for more widespread use in controlling other symptoms of skin cancer. In the case of immunotherapy (biologic treatment), a patient's natural immune system is raised or other immune compositions (IL-2) are administered to the patient against the cancer.

"Metastatic melanoma" refers to a progressed form of melanoma wherein the original cancer has metastasized to another area of the skin (regional or distant) or to other non-skin tissue (e.g., lungs, liver, brain, lymph system). Metastatic melanoma describes when melanoma has spread into surrounding healthy tissue and through the bloodstream, or lymphatic system, to other parts of the body. If melanoma spreads to these other areas, the cancer cells in the new tumor are still melanoma cells but the disease is called metastatic melanoma.

Unlike early stages of melanoma, which can be treated successfully with early diagnosis, the prognosis for patients diagnosed with metastatic melanoma is poor, with survival rates of six to nine months. In the past 35 years, the FDA has only approved two types of therapies for metastatic melanoma interleukin 2 (IL-2) and DTIC. The methods of treatment for metastatic melanoma include radiation, immunotherapy, chemotherapy and palliative surgery. Currently, there are no approved therapies that significantly improve survival for patients with metastatic melanoma.

The term "imaging", "molecular imaging" or "radioimaging is used to describe methods that use the nuclear properties of matter in diagnosis and therapy, pursuant to the present invention. More specifically, the present invention relies on molecular imaging because it produces images that reflect biological processes that take place at the cellular and subcellular level.

Molecular imaging is a discipline that unites molecular biology and in vivo imaging. It enables the visualisation of the cellular function and the follow-up of the molecular process in living organisms without perturbing them. The multiple and numerous potentialities of this field are applicable to the diagnosis and treatment of diseases such as cancer, in the present invention, in particular, melanoma, including metastatic melanoma. This technique also contributes to improving the treatment of these disorders by optimizing the pre-clinical and clinical tests of new medication. This approach also has a major economic impact due to earlier and more precise diagnosis.

Molecular imaging differs from traditional imaging in that probes labeled biomarkers are used to help image particular targets or pathways. Biomarkers interact chemically with their surroundings and in turn alter the image according to molecular changes occurring within the area of interest. This process is markedly different from previous methods of imaging which primarily imaged differences in qualities such as density or water content. This ability to image fine molecular changes opens up an incredible number of exciting possibilities for medical application, including early detection and treatment of disease, in particular, melanoma and metastatic melanoma according to the present invention.

There are a number of different imaging modalities that can be used for noninvasive molecular imaging, using compounds according to the present invention. Each has different strengths and weaknesses and some are more adept at imaging multiple targets or sites than others. This is important in instances where metastatic melanoma is suspected. The modalities which can be used in the present invention are varied and in the present invention principally include single photon emission computed tomography (SPECT) and positron emission tomography (PET), discussed below.

The main purpose of SPECT when used in melanoma imaging pursuant to the present invention is to measure the distribution of radioisotope in skin tissue, in particular, those skin regions and other tissues where melanoma, including metastatic melanoma, is suspected. The development of computed tomography in the 1970s allowed mapping of the distribution of the radioisotopes in tissue, and led to the technique now called SPECT.

The imaging agent used in SPECT emits gamma rays, as opposed to the positron emitters used in PET. There are a number of radioisotopes (such as $^{99m}Tc$, $^{111}In$, $^{123}I$, $^{201}Tl$, $^{67}Ga$, $^{99m}Tc$ and $^{203}Pb$, among other gamma ray emitters) that can be used in the present invention and imaged with SPECT technology. In SPECT, where possible, by rotating the gamma camera around the area to be analysed, a three dimensional image of the distribution of the radiotracer may be obtained by employing filtered back projection or other tomographic techniques. The radioisotopes used in SPECT have relatively long half lives (a few hours to a few days) making them easy to produce and relatively cheap in comparison to other radioisotopes. This represents the major advantage of SPECT as an imaging technique, since it is significantly cheaper than PET or other imaging methods such as magnetic resonance imaging (MRI). However, SPECT sometimes lacks exceptional spatial (i.e., where exactly the particle is) or temporal (i.e., did the contrast agent signal happen at a particular millisecond or not) resolution.

Another imaging technique which finds particular use in the present invention is positron emission tomography (PET). In PET, a molecule is tagged with a positron emitting isotope. These positrons (βparticles) interact with nearby electrons, emitting two 511,000 eV photons, directed 180 degrees apart in opposite directions. These photons are then detected by the scanner which can estimate the density of positron annihilations in a specific area. When enough interactions and annihilations have occurred, the density of the original molecule may be measured in that area. Typical isotopes include $^{11}C$, $^{13}N$, $^{15}O$, $^{18}F$, $^{64}Cu$, $^{62}Cu$, $^{124}I$, $^{76}Br$, $^{82}Rb$ and $^{68}Ga$, among others, including the preferred $^{66}Ga$, $^{68}Ga$, $^{64}Cu$, $^{86}Y$. One of the major disadvantages of PET is that most of the radioisotopes must be made with a cyclotron, thus making the use of PET, in certain instances prohibitively expensive. Most of these probes also have a half life measured in minutes and hours, thus forcing the cyclotron, in many instances, to be on site. These factors can make PET sometimes prohibitively expensive, except in certain cases, which the present invention addresses in certain aspects. PET imaging does have many advantages though. First and foremost is its sensitivity: a typical PET scanner can detect between $10^{-11}$ mol/L to $10^{-12}$ mol/L concentrations.

The term "effective" is used, to describe an amount of a compound, component or composition, which produces an intended effect when used within the context of its use, which may be a diagnostic method, a therapeutic method, a method to monitor the progression of therapy or other method (chemical synthesis) pursuant to the present invention. In the case of therapeutic methods, an effective amount for treating melanoma, including metastatic melanoma, is that amount which shrinks cancerous tissue (e.g., tumor), produces a remission, prevents further growth of the tumor and/or reduces the likelihood that the cancer in its early stages (in situ or invasive) does not progress further to metastatic melanoma. In preferred therapeutic aspects of the invention, the radioisotopes $^{186}Re$ and $^{188}Re$ are complexed to the cyclic peptide compounds according to the present invention to produce unexpectedly effective therapeutic agents for the treatment of melanoma, including metastatic melanoma according to the present invention.

Noted here is that within the context of the use of the present invention, the patient will be receiving a radiation dose, which provides guidance to the amount of compound which is considered effective when used within the context of its use. A patient undergoing a nuclear medicine procedure will receive a radiation dose. Under present international guidelines it is assumed that any radiation dose, however small, presents a risk. The radiation doses delivered to a patient in a nuclear medicine investigation present a very small risk of side effects, including inducing cancer in the patient. In this respect it is similar to the risk from X-ray investigations except that the dose is delivered internally rather than from an external source such as an X-ray machine.

The radiation dose from a diagnostic nuclear medicine procedure is expressed as an effective dose with units of sieverts (usually given in millisieverts, mSv). The effective dose resulting from an investigation is influenced by the amount of radioactivity administered in megabecquerels (MBq), the physical properties of the radiopharmaceutical used, its distribution in the body and its rate of clearance from the body.

Effective doses can range from 6 μSv (0.006 mSv) for a 3 MBq chromium-51 EDTA measurement of glomerular filtration rate to 37 mSv or more for a 150 MBq thallium-201 non-specific tumour imaging procedure. The common bone scan with 600 MBq of technetium-99m-MDP has an effective dose of 3 mSv. Formerly, units of measurement were the Curie (Ci), being 3.7E10 Bq, and also 1.0 grams of radium (Ra-226); the rad (radiation absorbed dose), now replaced by the Gray; and the rem (röntgen equivalent man), now replaced with the Sievert. The rad and rem are essentially equivalent for almost all nuclear medicine procedures, and only alpha radiation will produce a higher Rem or Sv value, due to its much higher relative biological effectiveness (RBE).

The term "coadministration" or "combination therapy" is used to describe a therapy in which at least two active compounds (one of which is a compound according to the present invention) in effective amounts are used to treat melanoma, including metastatic melanoma as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more compounds including a chemotherapeutic agent such as dacarbazine (DTIC) or other anticancer agent useful in the treatment of melanoma and/or and immunotherapeutic agent such as IL-2 and/or α-interferon, among other compounds.

The term "treating" or "successfully treating" when used within the context of treating melanoma, including metastatic melanoma, shall include shrinking a tumor, curing melanoma, including melanoma which has metastasized (by causing a remission of the cancer in the patient) or reducing the likelihood or preventing the spread of the melanoma into other organs. Melanoma, including metastatic melanoma, may be treated using compounds according to the present invention alone, or in combination with other methods and/or compounds including surgery, chemotherapy (especially the use of the chemotherapeutic agent dacarbazine or DTIC or a related anticancer agent), radiation therapy (i.e., with agents other than the present therapeutic compositions) and immunotherapy (IL-2 and/or α-interferon).

In preferred aspects, $R_i$ is selected from the group consisting of $^{111}$In, $^{86}$Y, $^{66}$Ga, $^{67}$Ga, $^{68}$Ga, $^{203}$Pb, $^{64}$Cu and $^{99m}$Tc when the compounds are to be used diagnostically or to monitor therapeutic intervention and $R_f$ is selected from the group consisting of $^{90}$Y, $^{177}$Lu, $^{186}$Re, $^{188}$Re, $^{212}$Bi/$^{212}$Pb, $^{213}$Bi, $^{149}$Pm, $^{166}$Ho and $^{153}$Sm when compounds according to the present invention are used in radiation therapy to treat melanoma, including metastatic melanoma. Often, isotopes for use in therapy to treat melanoma, including metastatic melanoma include $^{186}$Re and $^{188}$Re.

The present invention also relates to pharmaceutical compositions comprising an effective amount of a compound for diagnostic and/or therapeutic purposes in combination with a pharmaceutically acceptable carrier, additive or excipient in pharmaceutical dosage form. For diagnostic purposes pharmaceutical compositions are formulated generally in parenteral dosage form, especially for intravenous administration, although oral or topical formulations may be useful in certain instances. In the case of the use of compounds according to the present invention for therapeutic purposes, the compositions are formulated preferably in parenteral or topical dosage forms, although orally administered dosage forms are also useful.

The compounds of the present invention, may, in accordance with the invention, be administered in single or divided doses by oral, parenteral or topical routes. Administration of the active compound may range from a single intravenous injection to continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present invention as sprays, mists, or aerosols for intra-nasal, intratracheal or pulmonary administration may also be used. The present invention therefore also is directed to pharmaceutical compositions comprising an effective amount of compound according to the present invention, optionally in combination with a pharmaceutically acceptable carrier, additive or excipient.

The amount of compound used is that amount effective within the context of the administration, whether that administration is for diagnostic purposes or therapeutic purposes. A suitable oral dosage for a compound according to the present invention would be in the range of about 0.01 mg to 10 g or more per day, preferably about 0.1 mg to about 1 g per day. In parenteral formulations, a suitable dosage unit may contain from 0.1 to 250 mg of said compounds, which may be administered from one to four times per day (for diagnostic purpose, preferably once in a bolus dose), whereas for topical administration, formulations containing 0.01 to 1% active ingredient are preferred. It should be understood, however, that the dosage administration from patient to patient will vary and the dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier, additive or excipient material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like.

The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose mannitol, methyl cellulose, microcrystalline cellulose, talc, silica, dibasic calcium phosphate, and high molecular weight polymers (such as polyethylene glycol).

For parenteral use, a compound according to the present invention can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds. In certain preferred diagnostic and/or therapeutic embodiments, compounds according to the present invention are administered intravenously in sterile saline solution.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Preservatives added may include benzalkonium chloride, chloro-butanol or phenylethyl alcohol, among numerous others.

Additionally, the compounds provided by the invention can be administered by suppository.

In certain aspects according to the present invention, where various cancers are to be treated, the compounds may be co-administered with at least one other anti-cancer agent such as dacarbazine (DTIC), among others, or an immunotherapeutic agent such as IL-2 and/or α-interferon. In addition, compounds according to the present invention may be administered prior to, during or after surgery to remove melanoma tissue.

Preparation of compounds according to the present invention proceeds using standard synthetic chemical techniques which are readily available in the art. Synthetic methods for obtaining compounds related to the present invention may be found in the examples section of the present specification. These methods can serve as guides for obtaining compounds according to the present invention. In general, the present compounds may be made by routine chemical synthesis of peptides using methods well known in the art. One can readily follow the synthetic methods described in the present specification with routine modification to provide all of the compounds described in the present application or using methods which are readily known in the art. The radionuclide is generally complexed to the oligopolypeptide after the oligo/polypeptide is synthesized, although alternative approaches to complexation can be used. Each of the two cyclic peptides (on the left- and right-side of the final compound) may be synthesized separately and then joined to each other by condensing onto or with the linker molecule (depending on the chemistry of the linker used). Cyclic peptide and/or the cyclic peptide with no linker is synthesized using conventional peptide synthesis (as otherwise described in the examples section or using methods readily available in the art using protecting group chemistry) and the various condensation and other reactions, etc. are readily performed using methods described herein or otherwise as readily known in the art. Other approaches will be readily recognized to those of ordinary skill.

Once the compounds are synthesized, they may be formulated in pharmaceutical dosage form using conventional pharmaceutical formulation methods readily available in the art by simply admixing compounds with chosen carriers, additives and/or excipients, depending upon the dosage form to be used and depending upon the use (diagnostic or therapeutic) of the compositions.

The following examples are provided to assist in describing the present invention. The details of these examples and the general description of the examples are for description purposes only and should be seen or taken to limit the scope of the invention in any way.

Examples

Chemicals and Reagents

Amino acid and resin were purchased from Advanced ChemTech Inc. (Louisville, Ky.) and Novabiochem (San Diego, Calif.). $^{125}$I-Tyr$^2$-[Nle$^4$, DPhe$^7$]-α-MSH {$^{125}$I-(Tyr$^2$)-NDP-MSH} was obtained from PerkinElmer, Inc. (Shelton, Conn.) for MC1 receptor binding assay. $^{99m}$TcO$_4^-$ was purchased from Cardinal Health (Albuquerque, N. Mex.) for peptide radiolabeling. All other chemicals used in this study were purchased from Thermo Fisher Scientific (Waltham, Mass.) and used without further purification. B16/F1 murine melanoma cells were obtained from American Type Culture Collection (Manassas, Va.).

MC1 Receptor Binding Affinity

The RAD-Lys-(Arg$^{11}$)CCMSH was synthesized according to our published procedure [23], purified by reverse phase-high performance liquid chromatography (RP-HPLC) and characterized by LC-mass spectroscopy. The IC$_{50}$ value of RAD-Lys-(Arg$^{11}$)CCMSH for the MC1 receptor was determined in B16/F1 melanoma cells. Briefly, the B16/F1 cells were harvested and seeded into a 24-well cell culture plate (0.2×10$^6$ cells/well) and incubated at 37° C. overnight. After being washed with binding medium {Modified Eagle's medium with 25 mM N-(2-hydroxyethyl)-piperazine-N'-(2-ethanesulfonic acid), pH 7.4, 0.2% bovine serum albumin (BSA), 0.3 mM 1,10-phenathroline}, the cells (n=3) were incubated at 25° C. for 2 h with approximately 30,000 counts per minute (cpm) of $^{125}$I-(Tyr$^2$) NDP-MSH in the presence of increasing concentrations (10$^{-13}$ to 10$^{-6}$ M) of the peptide in 0.3 mL of binding medium. The reaction medium was aspirated after the incubation. The cells were rinsed twice with 0.5 mL of ice-cold pH 7.4, 0.2% BSA/0.01 M phosphate buffered saline (PBS) and lysed in 0.5 mL of 1 N NaOH for 5 min. The radioactivities associated with cells were measured in a Wallac 1480 automated gamma counter (PerkinElmer, NJ). The IC$_{50}$ value of RAD-Lys-(Arg$^{11}$)CCMSH was calculated using the Prism software (GraphPad Software, La Jolla, Calif.).

Cellular Internalization and Efflux of $^{99m}$Tc-RAD-Lys-(Arg$^{11}$)CCMSH

RAD-Lys-(Arg$^{11}$)CCMSH was radiolabeled with $^{99m}$Tc using the method described previously [23]. The radiolabeled peptide was purified to single species by Waters RP-HPLC (Milford, Mass.) on a Grace Vydac C-18 reverse phase analytic column (Deerfield, Ill.) using a 20 min gradient of 16-26% acetonitrile in 20 mM HCl aqueous solution at a flow rate of 1 mL/min. Cellular internalization and efflux of $^{99m}$Tc-RAD-Lys-(Arg$^{11}$)CCMSH were evaluated in B16/F1 melanoma cells. Briefly, the B16/F1 cells in 24-well cell culture plates were incubated at 25° C. for 20, 40, 60, 90 and 120 min (n=4) in the presence of approximately 200,000 cpm of HPLC purified $^{99m}$Tc-RAD-Lys-(Arg$^{11}$)CCMSH. After incubation, the reaction medium was aspirated and the cells were rinsed twice with 0.5 mL of ice-cold pH 7.4, 0.2% BSA/0.01 M PBS. Cellular internalization of $^{99m}$Tc-RAD-Lys-(Arg$^{11}$) CCMSH was assessed by washing the cells with acidic buffer [40 mM sodium acetate (pH 4.5) containing 0.9% NaCl and 0.2% BSA] to remove the membrane-bound radioactivity. The remaining internalized radioactivity was obtained by lysing the cells with 0.5 mL of 1 N NaOH for 5 min. Membrane-bound and internalized $^{99m}$Tc activities were counted in a gamma counter. Cellular efflux of $^{99m}$Tc-RAD-Lys-(Arg$^{11}$)CCMSH was determined by incubating the B16/F1 cells with $^{99m}$Tc-RAD-Lys-(Arg$^{11}$)CCMSH for 2 h at 25° C., removing non-specific-bound radioactivity with 2×0.5 mL of ice-cold pH 7.4, 0.2% BSA/0.01 M PBS rinse, and monitoring radioactivity released into cell culture medium. At time points of 20, 40, 60, 90 and 120 min, the radioactivities in medium, on cell surface and in cells were separately collected and counted in a gamma counter.

Biodistribution Studies

All the animal studies were conducted in compliance with Institutional Animal Care and Use Committee approval. The biodistribution of $^{99m}$Tc-RAD-Lys-(Arg$^{11}$)CCMSH was determined in B16/F1 melanoma-bearing C57 mice (Harlan, Indianapolis, Ind.). C57 mice were subcutaneously inoculated on the right flank with 1×10$^6$ B16/F1 cells. Tumor weights reached approximately 0.2 g at 10 days post cell inoculation. Each melanoma-bearing mouse was injected with 0.037 MBq of $^{99m}$Tc-RAD-Lys-(Arg$^{11}$)CCMSH via the tail vein. Groups of 5 mice were sacrificed at 0.5, 2, 4 and 24 h post-injection, and tumors and organs of interest were harvested, weighed and counted. Blood values were taken as 6.5% of the whole-body weight.

The specificity of tumor uptake was determined at 2 h post-injection by co-injecting $^{99m}$Tc-RAD-Lys-(Arg$^{11}$)CCMSH with 10 µg (6.1 nmol) of unlabeled NDP-MSH. L-lysine co-injection is effective in decreasing the renal uptake of radiolabeled α-MSH peptides. To determine the effect of L-lysine co-injection on the renal uptake of $^{99m}$Tc-RAD-Lys-(Arg$^{11}$)CCMSH, a group of 5 mice were injected with a mixture of 0.037 MBq of $^{99m}$Tc-RAD-Lys-(Arg$^{11}$)CCMSH and 12 mg of L-lysine. The mice were sacrificed at 2 h post-injection, and tumors and organs of interest were harvested, weighed and counted in a gamma counter.

Melanoma Imaging and Urinary Metabolites of $^{99m}$Tc-RAD-Lys-(Arg$^{11}$)CCMSH Approximately 6.7 MBq of $^{99m}$Tc-RAD-Lys-(Arg$^{11}$)CCMSH was injected in a B16/F1 melanoma-bearing C57 mouse for imaging and urine analysis. The mouse was euthanized at 2 h post-injection for small animal SPECT/CT (Nano-SPECT/CT®, Bioscan) imaging, as well as to collect urine for analyzing the metabolites. The 9-min CT imaging was immediately followed by the whole-body SPECT scan. The SPECT scans of 24 projections were acquired. Reconstructed SPECT and CT data were visualized and co-registered using InVivoScope (Bioscan, Washington D.C.). The collected urine sample was centrifuged at 16,000 g for 5 min before the HPLC analysis. Thereafter, aliquots of the urine were injected into the HPLC. A 20-minute gradient of 16-26% acetonitrile/20 mM HCl with a flow rate of 1 mL/min was used for urine analysis.

Statistical Methods

Statistical analysis was performed using the Student's t-test for unpaired data to determine the significance of differences in tumor and kidney uptake between the groups in the biodistribution studies with/without peptide blockade or with/without L-lysine co-injection. Differences at the 95% confidence level (p<0.05) were considered significant.

Results

RAD-Lys-(Arg$^{11}$)CCMSH was synthesized, purified by RP-HPLC and characterized by electrospray ionization mass spectrometry. Schematic structure of RAD-Lys-(Arg$^{11}$)CCMSH is presented in FIG. 1. The structure of RGD-Lys-(Arg$^{11}$)CCMSH was cited from ref. 23 for comparison. The competitive binding curve of RAD-Lys-(Arg$^{11}$)CCMSH is presented in FIG. 2. The IC$_{50}$ value of RAD-Lys-(Arg$^{11}$)CCMSH was 0.26 nM in B16/F1 melanoma cells. The peptide was readily labeled with $^{99m}$Tc with greater than 90% radiolabeling yield. $^{99m}$Tc-RAD-Lys-(Arg$^{11}$)CCMSH was completely separated from its excess non-labeled peptide by RP-HPLC. The retention times of $^{99m}$Tc-RAD-Lys-(Arg$^{11}$)CCMSH and RAD-Lys-(Arg$^{11}$)CCMSH was 12.6 and 10.7 min, respectively. $^{99m}$Tc-RAD-Lys-(Arg$^{11}$)CCMSH showed greater than 99% radiochemical purity after HPLC purification.

Figure 3:
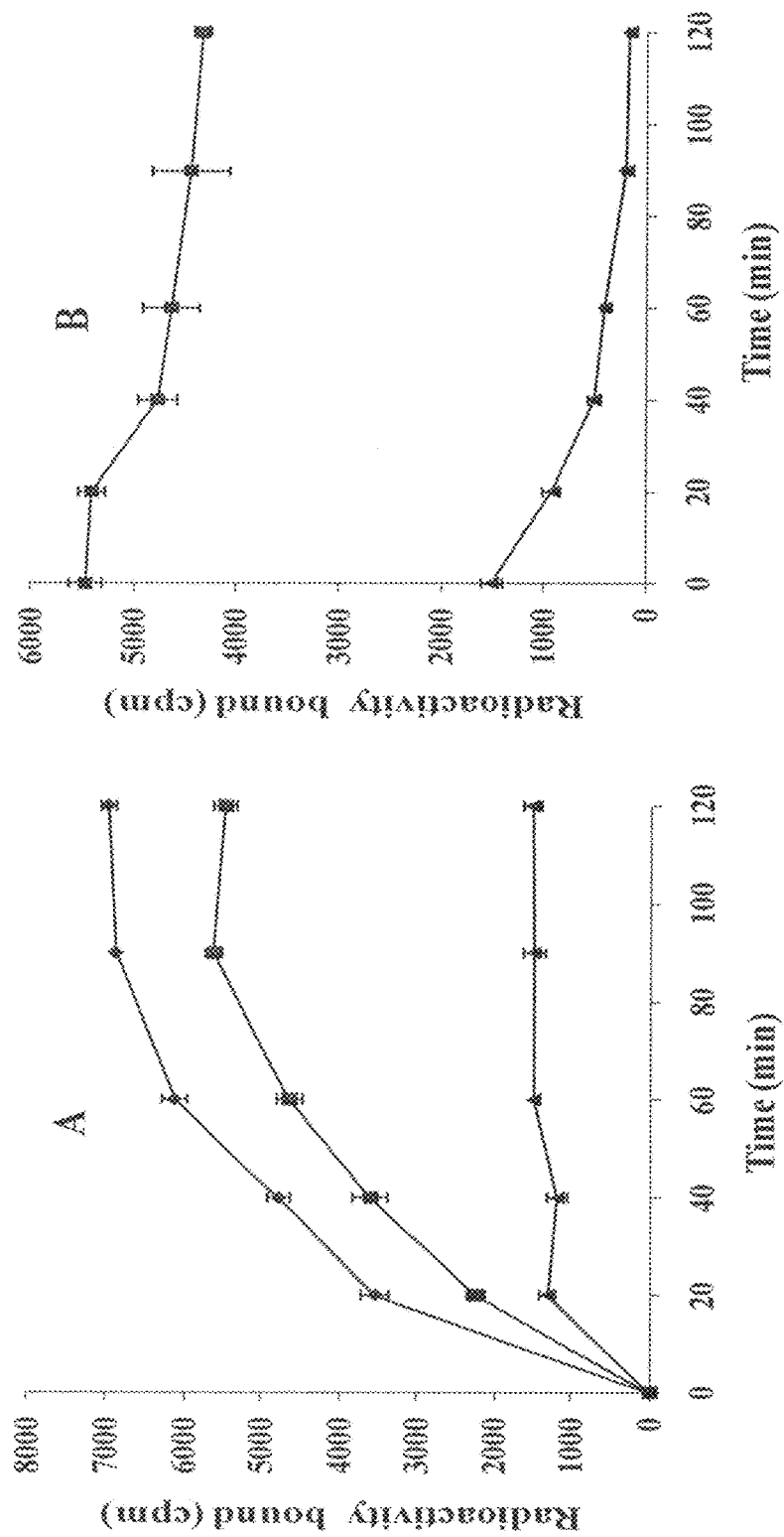
FIG. 3 shows the cellular internalization (A) and efflux (B) of $^{99m}$Tc-RAD-Lys-(Arg[11])CCMSH in B16/F1 melanoma cells. Total bound radioactivity (♦), internalized radioactivity (■) and cell membrane radioactivity (▲) were presented as counts per minute (cpm).

Cellular internalization and efflux of $^{99m}$Tc-RAD-Lys-(Arg$^{11}$)CCMSH in B16/F1 melanoma cells are presented in FIG. 3. $^{99m}$Tc-RAD-Lys-(Arg$^{11}$)CCMSH exhibited rapid cellular internalization and extended cellular retention. There was 59.20±5.10% of the $^{99m}$Tc-RAD-Lys-(Arg$^{11}$)CCMSH activity internalized at 20 min post incubation. There was 78.24±1.13% of the $^{99m}$Tc-RAD-Lys-(Arg$^{11}$)CCMSH activity internalized after 2 h incubation. The efflux results demonstrated that 79.44±3.61% of the $^{99m}$Tc-RGD-Lys-(Arg$^{11}$)CCMSH activity remained inside the cells 2 h after incubating cells in culture medium.

The melanoma targeting and pharmacokinetic properties of $^{99m}$Tc-RAD-Lys-(Arg$^{11}$)CCMSH were determined in B16/F1 melanoma-bearing C57 mice. The biodistribution results of $^{99m}$Tc-RAD-Lys-(Arg$^{11}$)CCMSH are shown in Table 1, FIG. 7. $^{99m}$Tc-RAD-Lys-(Arg$^{11}$)CCMSH exhibited rapid and high tumor uptake in melanoma-bearing mice. The tumor uptake was 16.65±1.91% ID/g at 0.5 h post-injection. $^{99m}$Tc-RAD-Lys-(Arg$^{11}$)CCMSH reached its peak tumor uptake of 19.91±4.02% ID/g at 2 h post-injection. There was 18.01±3.51% ID/g of the $^{99m}$Tc-RAD-Lys-(Arg$^{11}$)CCMSH activity remained in tumor at 4 h post-injection. The tumor uptake of $^{99m}$Tc-RAD-Lys-(Arg$^{11}$)CCMSH gradually decreased to 9.24±3.63% ID/g 24 h post-injection. In peptide blocking study, the tumor uptake of $^{99m}$Tc-RAD-Lys-(Arg$^{11}$)CCMSH with 10 µg (6.1 nmol) of non-radiolabeled NDP-MSH co-injection was only 7.8% of the tumor uptake without NDP-MSH co-injection at 2 h post-injection (p<0.01), demonstrating that the tumor uptake was specific and MC1 receptor-mediated. Whole-body clearance of $^{99m}$Tc-RGD-Lys-(Arg$^{11}$)CCMSH was rapid, with approximately 63% of the injected radioactivity cleared through the urinary system by 2 h post-injection (FIG. 7, Table 1) Normal organ uptake of $^{99m}$Tc-RGD-Lys-(Arg$^{11}$)CCMSH was generally low (<2.2% ID/g) except for kidneys after 2 h post-injection. High tumor/blood and tumor/muscle uptake ratios were demonstrated as early as 0.5 h post-injection (Figure, Table 1). The renal uptake of $^{99m}$Tc-RAD-Lys-(Arg$^{11}$)CCMSH reached its peak value of 127.41±17.32% ID/g at 0.5 h post-injection. The renal uptake decreased to 33.19±3.39% ID/g at 24 h post-injection. L-lysine co-injection significantly (p<0.05) reduced the renal uptake of $^{99m}$Tc-RAD-Lys-(Arg$^{11}$)CCMSH to 50.1±18.56% ID/g at 2 h post-injection without affecting the tumor uptake.

Figure 4:
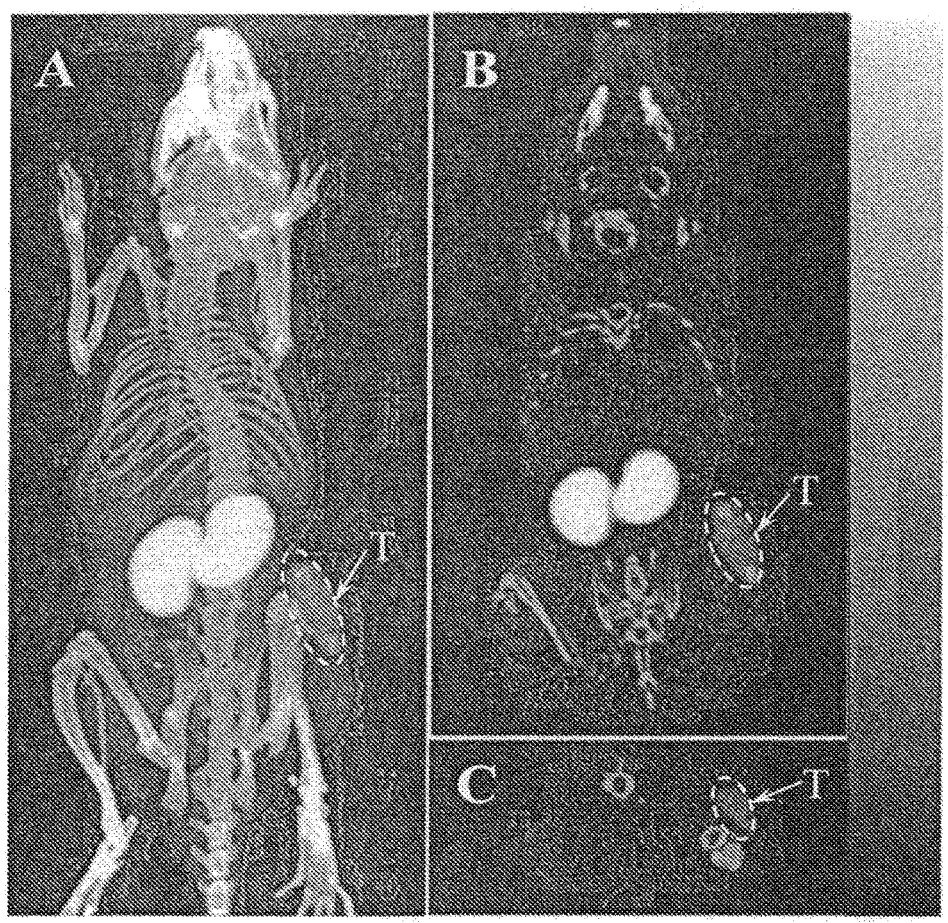
FIG. 4 shows the whole-body (A), coronal (B) and transversal (C) SPECT/CT images of $^{99m}$Tc-RAD-Lys-(Arg[11])CCMSH in a B16/F1 melanoma-bearing C57 mouse at 2 h post-injection.
Figure 5:
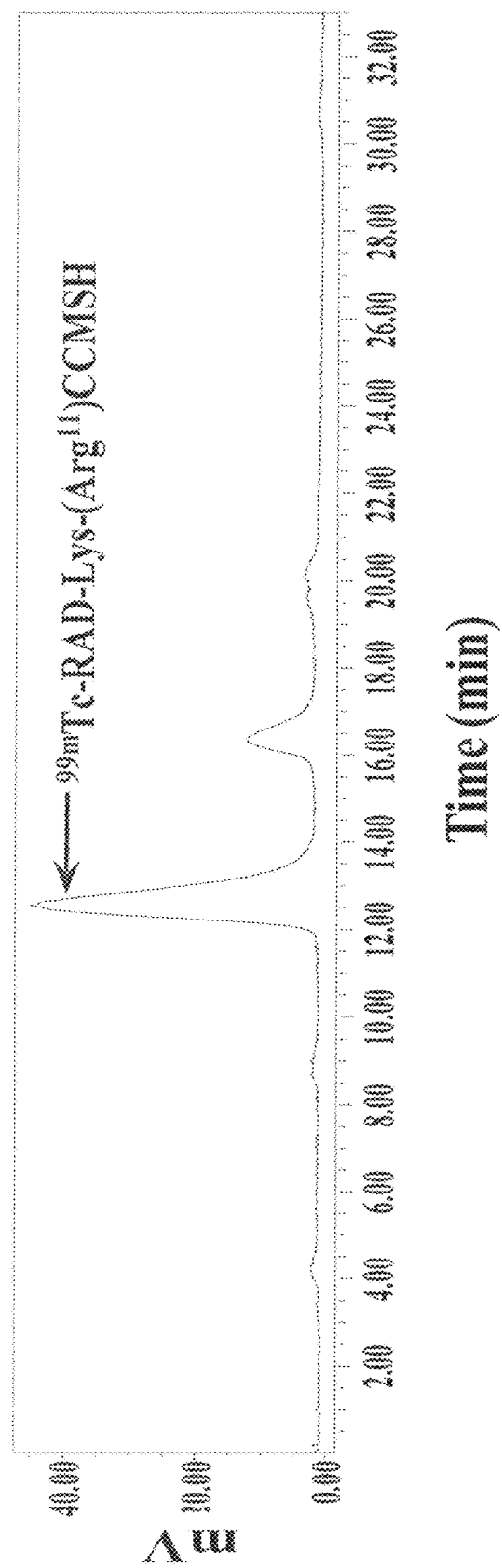
FIG. 5 shows the radioactive HPLC profile of urine sample of a B16/F1 melanoma-bearing C57 mouse at 2 h post-injection of $^{99m}$Tc-RAD-Lys-(Arg[11])CCMSH. Arrow indicates the retention time (12.6 min) of the original compound of $^{99m}$Tc-RAD-Lys-(Arg[11])CCMSH prior to the tail vein injection.

Melanoma imaging property of $^{99m}$Tc-RAD-Lys-(Arg$^{11}$)CCMSH was examined in a B16/F1 melanoma-bearing C57 mouse. The whole-body SPECT/CT image is presented in FIG. 4. Flank melanoma tumors were visualized clearly by $^{99m}$Tc-RAD-Lys-(Arg$^{11}$)CCMSH at 2 h post-injection. $^{99m}$Tc-RAD-Lys-(Arg$^{11}$)CCMSH exhibited high tumor to normal organ uptake ratios except for kidney. The urine collected from the imaging mouse was analyzed for the metabolites by HPLC. The urinary HPLC profile of $^{99m}$Tc-RAD-Lys-(Arg$^{11}$)CCMSH is shown in FIG. 5. Approximately 82% of $^{99m}$Tc-RAD-Lys-(Arg$^{11}$)CCMSH remained intact, whereas 18% of $^{99m}$Tc-RAD-Lys-(Arg$^{11}$)CCMSH was transformed to a more lipophilic metabolite at 2 h post-injection.

Discussion

The inventors successfully developed a novel $^{99m}$Tc-RGD-Lys-(Arg$^{11}$)CCMSH hybrid peptide to target both MC1 and α$_v$β$_3$ integrin receptors for M21 human melanoma imaging [23]. Both MC1 and α$_v$β$_3$ integrin receptors are over-expressed in M21 melanoma cells [23], making it a suitable melanoma cell line for evaluating dual receptor-targeting $^{99m}$Tc-RGD-Lys-(Arg$^{11}$)CCMSH hybrid peptide. It is known that the switch from the RGD to RAD sacrifices the binding affinity of the RGD to the $\alpha_v\beta_3$ integrin receptor. Not surprisingly, the switch from RGD to RAD in the hybrid peptide decreased the $\alpha_v\beta_3$ integrin receptor binding affinity of RAD-Lys-(Arg$^{11}$)CCMSH by 248-fold in M21 melanoma cells. Surprisingly, the inventors found that the switch from RGD to RAD in the hybrid peptide increased the MC1 receptor binding affinity of RAD-Lys-(Arg$^{11}$)CCMSH by 6.7-fold in M21 melanoma cells [23]. To investigate whether such change in MC1 receptor binding affinity could lead to enhanced melanoma uptake of $^{99m}$Tc-RAD-Lys-(Arg$^{11}$)CCMSH compared to $^{99m}$Tc-RGD-Lys-(Arg$^{11}$)CCMSH, we evaluated the receptor binding and melanoma targeting properties of $^{99m}$Tc-RAD-Lys-(Arg$^{11}$)CCMSH in B16/F1 melanoma cells and melanoma-bearing mice in this study. $^{99m}$Tc-RGD-Lys-(Arg$^{11}$)CCMSH targeted both MC1 and $\alpha_v\beta_3$ integrin receptors, whereas $^{99m}$Tc-RAD-Lys-(Arg$^{11}$)CCMSH only targeted the MC1 receptors. We chose B16/F1 melanoma cells for this study because only MC1 receptors (rather than $\alpha_v\beta_3$ integrin receptors) are over-expressed on B16/F1 cells [24]. Thus, selection of B16/F1 melanoma cells could minimize the contribution of $\alpha_v\beta_3$ integrin receptors to the melanoma uptake of dual receptor-targeting $^{99m}$Tc-RGD-Lys-(Arg$^{11}$)CCMSH.

Figure 2:
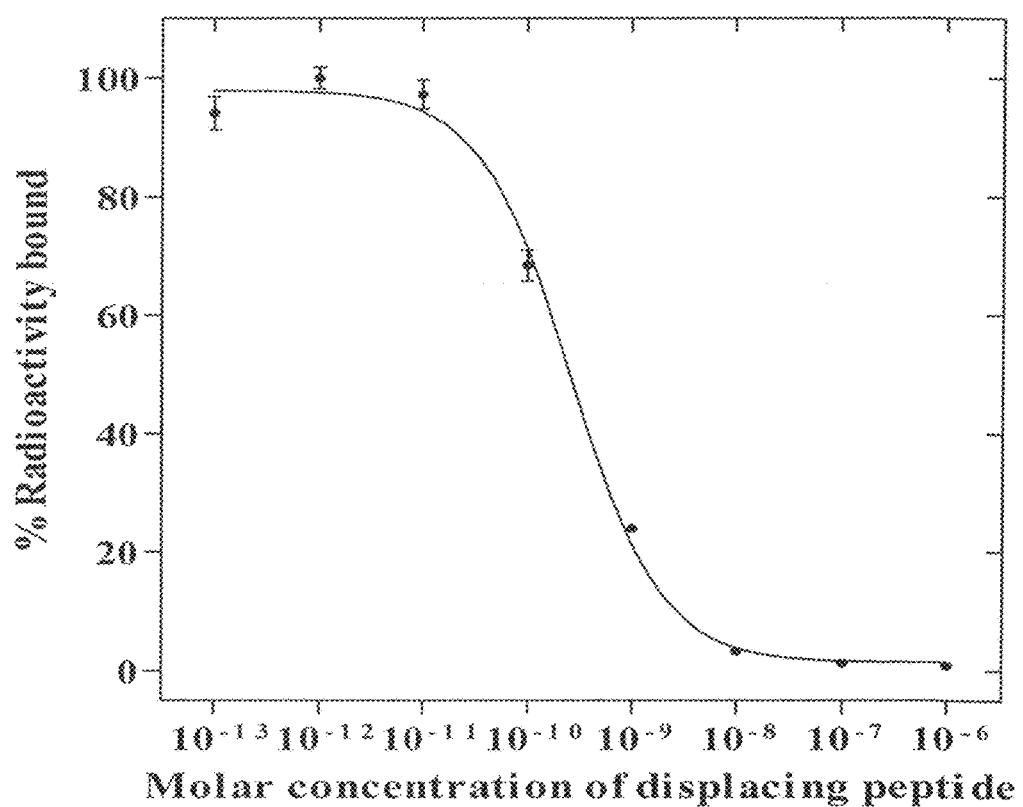
FIG. 2 shows the competitive binding curve of RAD-Lys-(Arg[11])CCMSH in B16/F1 melanoma cells. The IC$_{50}$ value of RAD-Lys-(Arg[11])CCMSH was 0.26 nM.

The structural difference between RAD-Lys-(Arg$^{11}$)CCMSH and RGD-Lys-(Arg$^{11}$)CCMSH was one more methyl group in Ala compared to Gly (FIG. 1). Despite such slight difference in structure, RAD-Lys-(Arg$^{11}$)CCMSH displayed much stronger MC1 receptor binding affinity than RGD-Lys-(Arg$^{11}$)CCMSH in B16/F1 melanoma cells. The MC1 receptor binding affinity of RAD-Lys-(Arg$^{11}$)CCMSH and RAD-Lys-(Arg$^{11}$)CCMSH was 0.26 and 2.1 nM in B16/F1 cells [24]. Although $^{99m}$Tc-RAD-Lys-(Arg$^{11}$)CCMSH displayed similar rapid internalization and extended retention pattern as $^{99m}$Tc-RGD-Lys-(Arg$^{11}$)CCMSH, more $^{99m}$Tc-RAD-Lys-(Arg$^{11}$)CCMSH activity was internalized and remained in B16/F1 melanoma cells.

$^{99m}$Tc-RGD-Lys-(Arg$^{11}$)CCMSH displayed a rapid B16/F1 melanoma uptake of 11.06±1.41% ID/g at 0.5 h post-injection and reached its peak tumor uptake of 14.83±2.94% ID/g at 2 h post-injection in our previous report [24]. The tumor uptake of $^{99m}$Tc-RGD-Lys-(Arg$^{11}$)CCMSH was 12.57±2.53 and 7.59±2.04% ID/g at 4 h and 24 h post-injection, respectively [24]. In this study, the switch from RGD to RAD significantly (p<0.05) improved the tumor uptake of $^{99m}$Tc-RAD-Lys-(Arg$^{11}$)CCMSH at 0.5, 2 and 4 h post-injection. The tumor uptake of $^{99m}$Tc-RAD-Lys-(Arg$^{11}$)CCMSH was 1.51, 1.34 and 1.43 times the tumor uptake of $^{99m}$Tc-RGD-Lys-(Arg$^{11}$)CCMSH at 0.5, 2 and 4 h post-injection (FIG. 6A), respectively. The improved melanoma uptake of $^{99m}$Tc-RAD-Lys-(Arg$^{11}$)CCMSH was likely due to its stronger MC1 receptor binding affinity compared to $^{99m}$Tc-RGD-Lys-(Arg$^{11}$)CCMSH (0.26 vs. 2.1 nM). Meanwhile, the replacement of the RGD motif with RAD significantly (p<0.05) decreased the liver uptake of $^{99m}$Tc-RAD-Lys-(Arg$^{11}$)CCMSH at 0.5, 4 and 24 h post-injection. The liver uptake of $^{99m}$Tc-RAD-Lys-(Arg$^{11}$)CCMSH was 66.2, 61.9 and 72.3% of the liver uptake of $^{99m}$Tc-RGD-Lys-(Arg$^{11}$)CCMSH at 0.5, 2 and 24 h post-injection (FIG. 6B), respectively.

Figure 6:
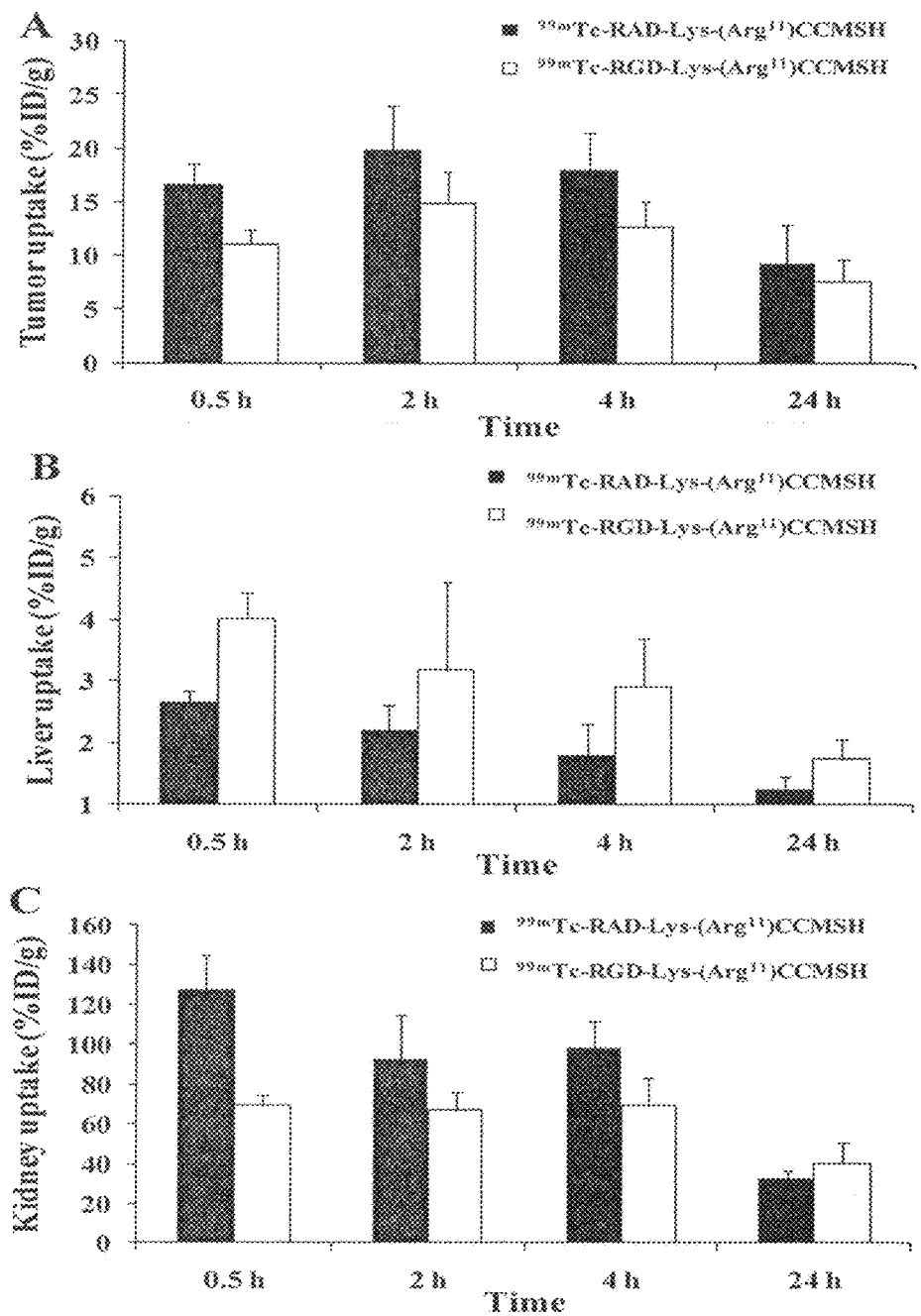
FIG. 6 shows the comparison in tumor, liver and kidney uptake between $^{99m}$Tc-RAD-Lys-(Arg[11])CCMSH and $^{99m}$Tc-RGD-Lys-(Arg[11])CCMSH. The data of $^{99m}$Tc-RGD-Lys-(Arg[11])CCMSH was cited from ref. 24.

B16/F1 melanoma lesions were clearly visualized by SPECT/CT imaging using $^{99m}$Tc-RAD-Lys-(Arg$^{11}$)CCMSH as an imaging probe 2 h post injection, highlighting the potential use of $^{99m}$Tc-RAD-Lys-(Arg$^{11}$)CCMSH for melanoma imaging. $^{99m}$Tc-RGD-Lys-(Arg$^{11}$)CCMSH displayed high tumor to normal organ uptake ratios except for kidney, which was coincident with the biodistribution results (Table 1). As shown in FIG. 6C, $^{99m}$Tc-RAD-Lys-(Arg$^{11}$)CCMSH exhibited significantly higher renal uptake than that of $^{99m}$Tc-RGD-Lys-(Arg$^{11}$)CCMSH at 0.5, 2 and 4 h post-injection. The renal uptake of $^{99m}$Tc-RAD-Lys-(Arg$^{11}$)CCMSH was 1.84, 1.39 and 1.42 times the renal uptake of $^{99m}$Tc-RGD-Lys-(Arg$^{11}$)CCMSH at 0.5, 2 and 4 h post-injection, respectively. Co-injection of peptide blockade did not reduce the renal uptake, indicating that the renal uptake of $^{99m}$Tc-RAD-Lys-(Arg$^{11}$)CCMSH was not MC1 receptor-mediated. L-lysine co-injection significantly decreased the renal uptake of $^{99m}$Tc-RAD-Lys-(Arg$^{11}$)CCMSH by 46%, demonstrating that L-lysine co-injection could be used to reduce the renal uptake of $^{99m}$Tc-RAD-Lys-(Arg$^{11}$)CCMSH. Importantly, the success of L-lysine co-injection suggested that the positive charge played a key role in the renal uptake of $^{99m}$Tc-RAD-Lys-(Are)CCMSH. It was worthwhile to note that the epsilon amino group of Lys linking the RAD motif and CCMSH contributed a positive charge to the overall charge of $^{99m}$Tc-RAD-Lys-(Arg$^{11}$)CCMSH. Reduction of the overall positive charge of radiolabeled α-MSH peptide via structural modification has been successfully utilized to decrease the renal uptake by 50% [11]. Accordingly, it would be likely to decrease the renal uptake of $^{99m}$Tc-RAD-Lys-(Arg$^{11}$)CCMSH by substituting the Lys linker with neutral amino acid or polyethylene glycol (PEG) linker in our future studies.

CONCLUSIONS

The switch from RGD to RAD significantly enhanced the melanoma uptake of $^{99m}$Tc-RAD-Lys-(Arg$^{11}$)CCMSH compared to $^{99m}$Tc-RGD-Lys-(Arg$^{11}$)CCMSH in B16/F1 melanoma-bearing C57 mice. B16/F1 melanoma lesions were clearly visualized by SPECT/CT imaging using $^{99m}$Tc-RAD-Lys-(Arg$^{11}$)CCMSH as an imaging probe, highlighting its potential use as an imaging probe for melanoma detection as well as therapeutics.

REFERENCES

[1] Jemal A, Siegel R, Xu J, Ward E. Cancer statistics. CA Cancer J Clin 2010; 60:277-300.

[2] Giblin M F, Wang N, Hoffman T J, Jurisson S S, Quinn T P. Design and characterization of alpha-melanotropin peptide analogs cyclized through rhenium and technetium metal coordination. Proc Natl Acad Sci USA 1998; 95:12814-8.

[3] Froidevaux S, Calame-Christe M, Tanner H, Sumanovski L, Eberle A N. A novel DOTA-alpha-melanocyte-stimulating hormone analog for metastatic melanoma diagnosis. J Nucl Med 2002; 43:1699-706.

[4] Miao Y, Whitener D, Feng W, Owen N K, Chen J, Quinn T P. Evaluation of the human melanoma targeting properties of radiolabeled alpha-melanocyte stimulating hormone peptide analogues. Bioconjug Chem 2003; 14:1177-84.

[5] Froidevaux S, Calame-Christe M, Schuhmacher J, Tanner H, Saffrich R, Henze M. et al. A gallium-labeled DOTA-alpha-melanocyte-stimulating hormone analog for PET imaging of melanoma metastases. J Nucl Med 2004; 45:116-23.

[6] McQuade P, Miao Y. Yoo J, Quinn T P, Welch M J, Lewis J S. Imaging of melanoma using $^{64}$Cu- and $^{86}$Y-DOTA-ReCCMSH(Arg$^{11}$), a cyclized peptide analogue of alpha-MSH. J Med Chem 2005; 48:2985-92.

[7] Wei L, Butcher C, Miao Y, Gallazzi F, Quinn T P, Welch M J, et al. Synthesis and biologic evaluation of $^{64}$Cu-labeled rhenium-cyclized alpha-MSH peptide analog using a cross-bridged cyclam chelator. J Nucl Med 2007; 48:64-72.

[8] Cheng Z, Xiong Z, Subbarayan M, Chen X, Gambhir S S. $^{64}$Cu-labeled alpha-melanocyte-stimulating hormone analog for MicroPET imaging of melanocortin 1 receptor expression. Bioconjug Chem 2007; 18:765-72.

[9] Miao Y, Benwell K, Quinn T P. $^{99m}$Tc- and $^{111}$In-labeled alpha-melanocyte-stimulating hormone peptides as imaging probes for primary and pulmonary metastatic melanoma detection. J Nucl Med 2007; 48:73-80.

[10] Miao Y, Figueroa S D, Fisher D R, Moore H A, Testa R F, Hoffman T J, et al. $^{203}$Pb-labeled alpha-melanocyte-stimulating hormone peptide as an imaging probe for melanoma detection. J Nucl Med 2008; 49:823-9.

[11] Miao Y, Gallazzi F, Guo H, Quinn T P. $^{111}$In-labeled lactam bridge-cyclized alpha-melanocyte stimulating hormone peptide analogues for melanoma imaging. Bioconjug Chem 2008; 19:539-47.

[12] Guo H, Shenoy N, Gershman B M, Yang J, Sklar L A, Miao Y. Metastatic melanoma imaging with an $^{111}$In-labeled lactam bridge-cyclized alpha-melanocyte stimulating hormone peptide. Nucl Med Biol 2009; 36:267-76.

[13] Guo H, Yana J, Gallazzi F, Miao Y. Reduction of the ring size of radiolabeled lactam bridge-cyclized alpha-MSH peptide resulting in enhanced melanoma uptake. J Nucl Med 2010; 51:418-26.

[14] Guo H, Yang J, Gallazzi F, Miao Y. Effects of the amino acid linkers on melanoma-targeting and pharmacokinetic properties of Indium-111-labeled lactam bridge-cyclized α-MSH peptides. J Nucl Med 2011; 52:608-16.

[15] Haubner R, Wester H J, Reuning U, Senekowitsch-Schmidtke R, Diefenbach B, Kessler H, et al. Radiolabeled alpha(v)beta(3) integrin antagonists: a new class of tracers for tumor targeting. J Nucl Med 1999; 40:1061-71.

[16] Poethko T, Schottelius M, Thumshirn G, Hersel U, Herz M, Henriksen G, et al. Two-step methodology for high-yield routine radiohalogenation of peptides: $^{18}$F-labeled RGD and octreotide analogs. J Nucl Med 2004; 45:892-902.

[17] Li C, Wang W, Wu Q, Ke S, Houston J, Sevick-Muraca E, et al. Dual optical and nuclear imaging in human melanoma xenografts using a single targeted imaging probe. Nucl Med Biol 2006; 33:349-58.

[18] Decristoforo C, Faintuch-Linkowski B, Rey A, von Guggenberg E, Rupprich M, Hernandez-Gonzales I, et al. [$^{99m}$Tc]HYNIC-RGD for imaging integrin alphavbeta3 expression. Nucl Med Biol 2006; 33:945-52.

[19] Alves S, Correia J D, Gano L, Rold T L, Prasanphanich A, Haubner R, et al. In vitro and in vivo evaluation of a novel $^{99m}$Tc(CO)$_3$-pyrazolyl conjugate of cyclo-(Arg-Gly-Asp-d-Tyr-Lys). Bioconjug Chem 2007; 18:530-7.

[20] Decristoforo C, Hernandez Gonzalez I, Carlsen J, Rupprich M, Huisman M, Virgolini I, et al. $^{68}$Ga- and $^{111}$In-labelled DOTA-RGD peptides for imaging of alpha(v)beta(3) integrin expression. Eur J Nucl Med Mol Imaging 2008; 35:1507-15.

[21] Hultsch C, Schottelius M, Auernheimer J, Alke A, Wester H J. $^{18}$F-Fluoroglucosylation of peptides, exemplified on cyclo(RGDfK). Eur J Nucl Med Mol Imaging 2009; 36:1469-74.

[22] Wei L, Ye Y, Wadas T J, Lewis J S, Welch M J, Achilefu S, et al. $^{64}$Cu-labeled CB-TE2A and diamsar-conjugated RGD peptide analogs for targeting angiogenesis: comparison of their biological activity. Nucl Med Biol 2009; 36:277-85.

[23] Yana J, Guo H, Miao Y. Technetium-99m-labeled Arg-Gly-Asp-conjugated alpha-melanocyte stimulating hormone hybrid peptides for human melanoma imaging. Nucl Med Biol 2010; 37:873-83.

[24] Yang J. Guo H. Gallazzi F, Miao Y. Evaluation of a novel Arg-Gly-Asp-conjugated alpha-melanocyte stimulating hormone hybrid peptide for potential melanoma therapy. Bioconjug Chem 2009; 20:1634-42.

The invention claimed is:

1. A compound according to the chemical structure:

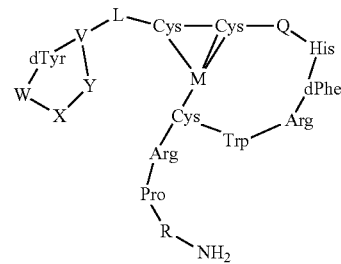

Where Q, V and W are each independently an amino acid unit selected from the group consisting of glutamic acid and aspartic acid;

R is an amino acid unit selected from the group consisting of valine, threonine, leucine, and isoleucine;

X is an amino acid residue selected from the group consisting of alanine, valine, threonine, leucine, isoleucine and serine;

Y is an amino acid residue selected from the group consisting of aspartic acid and glutamic acid;

L is alanine or a linker group according to the structure:

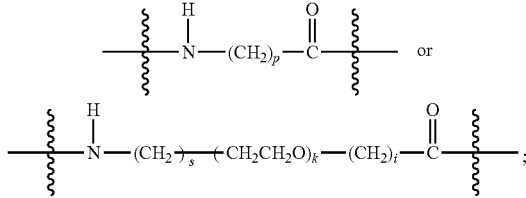

p is an integer from 0 to 20;

k is an integer from 1 to 10;

i is 1 or 2;

s is 0, 1 or 2; and

M is a radioisotope, or a pharmaceutically acceptable salt thereof.

2. The compound according to claim 1 wherein said radioisotope is a polyvalent cationic radioisotope selected from the group consisting of $^{86}$Y, $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re, and $^{99m}$Tc.

3. The compound according to claim 1 wherein X is alanine.

4. The compound according to claim 1 wherein said compound is

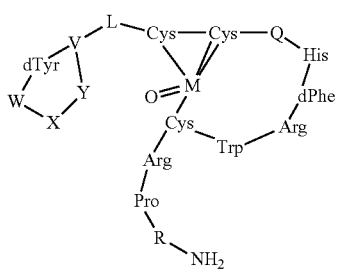

Where Q is glutamic acid;
R is valine;
V is aspartic acid;
W is aspartic acid;
X is alanine, valine, threonine, leucine or isoleucine;
Y is aspartic acid or glutamic acid;
p is an integer from 0-6;
k is 1 or 2;
i is 1;
s is 0; and
M is $^{99m}$Tc, $^{188}$Re or $^{186}$Re; or
a pharmaceutically acceptable salt thereof.

5. The compound according to claim 1 wherein L is

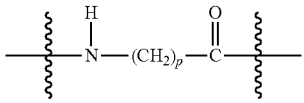

and p is 1-6.

6. The compound according to claim 1 wherein L is

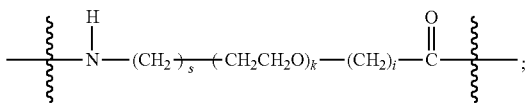

s is 0 and i is 1; and
k is 1-5.

7. The compound according to claim 1 wherein M is $^{99m}$Tc, $^{188}$Re or $^{186}$Re.

8. A method of diagnosing melanoma in a patient suspected of having melanoma comprising administering to said patient an effective amount of a compound according to claim 1 and determining whether said compound has bound to tissue in said patient which evidences the existence of a melanoma tumor in said tissue when compared to a standard.

9. The method according to claim 8 wherein said radioisotope M is a polyvalent cationic radioisotope selected from the group consisting of $^{86}$Y, $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re, and $^{99m}$Tc.

10. The method according to claim 8 wherein X is alanine.

11. A method of treating melanoma in a patient in need thereof comprising administering to said patient an effective amount of a compound according to claim 1, wherein said radioisotope is $^{90}$Y, $^{177}$Lu, $^{225}$Ac, $^{212}$Bi, $^{213}$Bi, $^{66}$Ga, $^{67}$Cu, $^{212}$Pb, $^{166}$Ho, $^{149}$Pm, $^{153}$Sm, $^{188}$Re, $^{186}$Re, $^{76}$As or $^{77}$As.

12. The method according to claim 11 wherein said compound is administered in topical dosage form.

13. The method according to claim 12 wherein said compound is administered directly onto melanoma tissue on the skin.

14. The method according to claim 11 wherein said compound is administered in parenteral dosage form.

15. The method according to claim 11 wherein said melanoma is metastatic melanoma.

16. A pharmaceutical composition comprising an effective amount of a compound according to claim 1 in combination with a pharmaceutically acceptable carrier, additive or excipient.

17. The composition according to claim 16 in topical dosage form.

18. The composition according to claim 16 in parenteral dosage form.

19. A method of monitoring melanoma treatment in a patient being treated for melanoma comprising administering a compound according to claim 1 to said patient, and diagnosing melanoma in said patient during the course of said treatment by measuring the extent of binding of said compound to melanoma tissue in said patient, wherein a decrease in melanoma tissue evidenced by reduced binding of said compound to said melanoma tissue in said patient during the course of said treatment is evidence of success of said treatment.

* * * * *